United States Patent [19]
Pell

[11] Patent Number: 5,713,348
[45] Date of Patent: Feb. 3, 1998

[54] ENDOTRACHEAL TUBE CONNECTOR AND METHOD FOR OPTIMIZING THE BREATHING ABILITY OF AN INTUBATED PATIENT

[76] Inventor: Donald M. Pell, P.O. Box 31647, St. Petersburg, Fla. 33732-1647

[21] Appl. No.: 725,034

[22] Filed: Oct. 2, 1996

[51] Int. Cl.$^6$ ........................................... A62B 9/04
[52] U.S. Cl. ................... 128/202.27; 128/207.14; 128/912
[58] Field of Search ............... 128/207.14, 207.15, 128/207.16, 912, 725, 202.27

[56] References Cited

U.S. PATENT DOCUMENTS

| | | | |
|---|---|---|---|
| 4,158,360 | 6/1979 | Adams | 128/725 |
| 4,444,201 | 4/1984 | Itoh | 128/725 |
| 4,723,543 | 2/1988 | Beran | 128/725 |
| 4,739,987 | 4/1988 | Nicholson | 128/207.16 |
| 4,774,945 | 10/1988 | White et al. | 128/207.16 |
| 4,852,582 | 8/1989 | Pell | 128/725 |
| 4,919,127 | 4/1990 | Pell | 128/207.14 |
| 4,984,158 | 1/1991 | Hillsman | 128/725 |
| 5,193,532 | 3/1993 | Moa et al. | 128/912 |
| 5,611,336 | 3/1997 | Page et al. | 128/207.16 |

*Primary Examiner*—Aaron J. Lewis
*Attorney, Agent, or Firm*—David E. Dougherty, Esq.

[57] ABSTRACT

A method for optimizing the breathing ability of an intubated patient is based on an evaluation of the expirational flow characteristics of an endotracheal tube connector. It has been found that an increase in the amount of work required for the expirational portion of the breathing cycle while minimizing the inspirational work of a patient improves the patient's blood chemistry and the absorption of oxygen and/or medication by the lung.

The method may be obtained by using an improved connector which includes an annular gas inlet and an annular gas outlet which share a common longitudinal axis. The inlet has an inside diameter which is about 2-½ to 3 times greater than the inside diameter of the outlet and is adapted to receive a flexible tube having an outside diameter which is approximately the same as the inside diameter inserted therein. The use of a shortened annular gas inlet which has a length which is less than its diameter, and preferably about ¼ to ⅓ of its diameter, slightly increases the work of expiration.

13 Claims, 2 Drawing Sheets

ENDOTRACHEAL TUBE CONNECTOR AND METHOD FOR OPTIMIZING THE BREATHING ABILITY OF AN INTUBATED PATIENT

FIELD OF THE INVENTION

The present invention relates to an endotracheal tube connector for connecting an endotracheal tube to a source of oxygen and, more particularly, to an endotracheal tube connector having a relatively large gas inlet and a generally funnel-shaped portion for reducing the inspirational work of an intubated patient and means for increasing the expirational work by the intubated patient. The invention also relates to a method for optimizing the breathing ability of an intubated patient based on an evaluation of the expirational flow characteristics of an endotracheal tube connector.

BACKGROUND OF THE INVENTION

Prior art endotracheal tube connectors which are in common use have a common configuration. For example, the configuration consists basically of a pair of cylindrical barrels which share a common longitudinal axis. The first barrel, i.e., the gas inlet, has an outside diameter of about 15 mm and is adapted to receive a flexible tube having an inside diameter of about 15 mm forced over the barrel for connecting the endotracheal tube to a source of oxygen.

The second barrel, or gas outlet, of the currently used connectors has an inside diameter of about 8 mm, which is the same as the inside diameter of an endotracheal tube. One end of the endotracheal tube, i.e., the end that protrudes from the mouth of a patient, is forced over the second barrel in order to insure an airtight fit, maximum gas flow and minimum resistance. In fact, the outside diameter of the outlet barrel is typically tapered at the patient end to facilitate insertion of the tubular member into the endotracheal tube and minimize turbulence as the gas passes from the connector into the endotracheal tube.

A number of problems with currently used configurations have arisen. For example, it is sometimes difficult to insert the connector into an endotracheal tube. Gupga U.S. Pat. No. 4,146,034 addresses this problem by providing a bevelled cut from the top of the connector to a point between the center line of the connector and the bottom thereof. Thus, the bevelled edge, taken together with the tapered portion, facilitates attaching the connector to an endotracheal tube and tends to minimize air turbulence as the gas flows from the connector into the endotracheal tube.

However, none of the previously mentioned prior art addressed the more serious problem which relates to the work of breathing with an endotracheal tube in place and the difficulty in removing seriously ill patients from a respirator. Removing a weakened patient from a respirator requires a patient to breathe on his or her own and overcome the resistance of the tube and the connector. Also, it is frequently necessary to have the patient inhale oxygen-enriched air and/or a gas containing medication. Apparently, the prior art devices overlooked a problem associated with minimizing obstructions and air turbulence at the inlet end of the connector as the oxygen-enriched air is pulled or inhaled into and through the connector.

My previous patent, U.S. Pat. No. 4,919,127, for an Endotracheal Tube Connector significantly reduced the work of breathing by reducing the negative pressure required to inhale a given volume of oxygen-enriched gas. Those connectors took optimizing advantage of the basic physical consideration to reduce, insofar as possible, the resistance to breathing for an intubated patient. In other words, such connectors reduced patient discomfort and trauma, and their use may avoid life-threatening consequences.

It has now been found that a further improvement over my earlier connector can be used for improving the breathing ability and treatment of an intubated patient. It has also been found that the improved connectors in accordance with the present invention can be readily used with most commercially available endotracheal tubes and are relatively inexpensive to produce and relatively easy to attach to an endotracheal tube and/or to a source of oxygen or medicated vapor, as selected by the physician. It has also been found that the combination of an endotracheal tube connector and T-shaped adapter, in accordance with the present invention, results in a dramatic reduction in the work for inspiration (inhaling) by a patient, as compared to the work which is required for a conventional connector-T-shaped adapter combination.

BRIEF SUMMARY OF THE INVENTION

In essence, the present invention contemplates a method for optimizing the breathing ability of an intubated patient. The method includes the steps of providing an endotracheal tube and a connector for connecting the endotracheal tube to a source of oxygen or other gas, and the step of intubating the patient with the endotracheal tube. The method also includes the further step of connecting the endotracheal tube to a source of oxygen or other gas by a connector which minimizes the inspirational work and, at the same time, slightly increases the expirational work of the patient.

In addition, the present invention contemplates a method for treating a patient by inserting an endotracheal tube into the patient's airway. The endotracheal tube is then connected to a source of oxygen or medicated gas, and the work of breathing is regulated to minimize the inspirational effort of the patient and, at the same time, increasing the expirational work of the patient which tends to maintain the oxygen and/or medicated gas within the patient's lungs for a longer period of time. In essence, it delays the expiration of the gas.

The invention also contemplates an improved connector which includes an annular gas inlet and an annular gas outlet sharing a common longitudinal axis with the inlet and with the outlet extending downstream from the inlet. The inlet has an inside diameter which is about 2-½ to 3 times greater than the inside diameter of the outlet and is adapted to receive a flexible tube having an outside diameter which is approximately the same as the inside diameter of the inlet inserted therein. An intermediate portion disposed between the inlet and the outlet defines a radially flared, outwardly extending, annular passageway which shares a common longitudinal axis with the inlet and the outlet. The radially flared, outwardly extending, annular passageway connects the inlet and the outlet with the smaller end of the radially flared passageway adjacent to the inside of the outlet. The connector also includes means for minimizing turbulence to thereby reduce the work of breathing, i.e., drawing a breath of air or other gas into the lungs. The means for minimizing turbulence includes a shoulder adjacent to the larger end of the radially flared passageway. The shoulder contributes to a reduction in turbulence, because it has a width approximately equal to the wall thickness of the flexible tube. Therefore, when the flexible tube is inserted into the inside of the inlet with its end abutting the shoulder, the outer edge of the large end of the radially flared passageway is flush with the interior passage provided by the flexible tube. This arrangement provides a smooth, relatively unobstructed, flow of gas through the tube and the connector. A patient end-portion of the outlet shares a common longitudinal axis with the cylindrical outlet means and extends downstream therefrom. The patient end-portion has a tapered outside diameter which terminates at a thin circular leading edge. This thin circular leading edge allows one end of the endotracheal tube, which extends outside of the patient, to be forced over the tapered portion to provide a relatively smooth, obstruction-free passageway from and through the connector to the endotracheal tube, whereby the work of inspiration by an intubated patient is minimized. The connector of the present invention also includes means for increasing the expirational work of breathing, i.e., the effort to force the inhaled gas out of the lungs. The means for increasing the expirational work of the patient resides in a shortened annular gas inlet which has a length which is less than its diameter and preferably between about ¼ to ⅓ of its diameter.

A preferred embodiment of the invention contemplates the combination of an endotracheal tube connector and a T-shaped adapter to significantly reduce the work of breathing for an intubated patient. In this embodiment, the connector includes an annular gas inlet and an annular gas outlet, which has a common longitudinal axis with the inlet. In this, and other embodiments, the outlet is defined as that portion of the connector which extends downstream from the inlet, i.e., as a patient inhales and thus draws the gas through the endotracheal tube and into the patient's lungs. The inlet has an inside diameter which is about 2.5 times greater than the inside diameter of the outlet and an intermediate portion between the inlet and outlet which defines a radially flared, outwardly extending annular passageway having a common longitudinal axis with the inlet and outlet. This annular passageway also connects the inlet and outlet with the smaller end of the flared passageway adjacent to the inside of the outlet. The combination, in accordance with a preferred embodiment of the invention, also includes a T-shaped adapter having a first portion (the cross member of the T) which defines a first cylindrical passageway extending therethrough. The adapter also includes a second portion (analogous to the vertical part of the T) which defines a second cylindrical passageway which intersects with or extends into the first cylindrical passageway. The second portion also includes coupling means for connecting the second portion of the T-shaped adapter to the inlet of the connector, with a relatively smooth transition for gas as it is drawn out of the T-shaped adapter and into and through the connector and endotracheal tube as a patient inhales. There is also a smooth transition as the patient exhales, and gas is forced back through the connector and T-shaped adapter.

The invention will now be described in connection with the accompanying drawings, wherein like reference numerals have been used to designate like parts.

DETAILED DESCRIPTION OF THE PREFERRED EMBODIMENTS OF THE INVENTION

Figure 2:
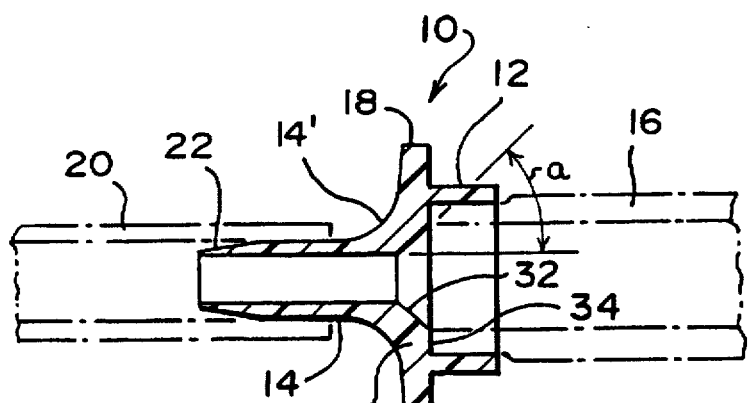
FIG. 2 is a cross-sectional view of the endotracheal tube connector shown in FIG. 1.
Figure 1:
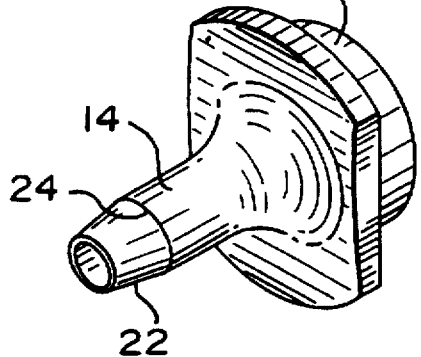
FIG. 1 is a perspective view of an endotracheal tube connector in accordance with a first embodiment of the invention.

Referring now to the drawings, FIGS. 1 and 2 illustrate an endotracheal tube connector according to a preferred embodiment of the invention. The connector 10 is an integral, one-piece element which includes a pair of cylindrically shaped tubular portions 12 and 14. The tubular or inlet portion 12 defines a gas passageway that may be referred to as the gas inlet or gas inlet portion, while portion 14, which also defines a gas passageway, may be referred to as the gas outlet or gas outlet portion. The two portions 12 and 14 share a common longitudinal axis and are aligned with the outlet portion 14 downstream from inlet portion 12.

The tubular portion 12, or gas inlet, has a relatively large inside diameter and is adapted to receive a flexible tube 16 having an outside diameter which is about the same as the inside diameter of portion 12. The flexible tube 16 is connected to a source of oxygen or other gas which is not shown in FIGS. 1 or 2. The flexible tube 16 is forced into the tubular portion 12 and forms an air-tight fit therewith.

Figure 3:
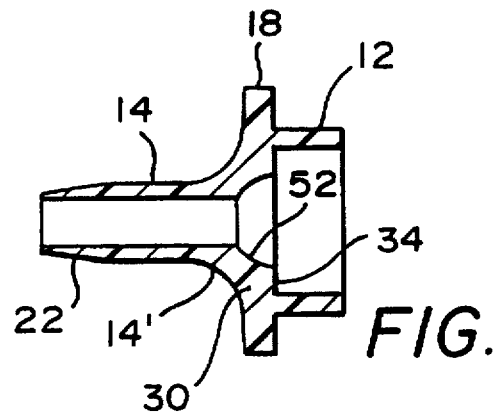
FIG. 3 is a cross-sectional view of an endotracheal tube connector in accordance with a second embodiment of the invention.

As illustrated in FIGS. 1, 2 and 3, the inlet portion 12 has a length or depth which is considerably less than or shorter than its diameter. The inlet portion 12 is also considerably shorter than the inlet portion of the connector, which is disclosed in my earlier U.S. Pat. No. , 4,919,127, which is incorporated herein in its entirety by reference. As shown therein, my earlier patent shows length of about ½ of its diameter. In the preferred embodiment of the present invention, the length of the inlet portion 12 is between about ¼ to ⅓ of its diameter.

The connector 10 also includes an outwardly extending flange 18 which is disposed between the tubular portions 12 and 14. The flange 18 has been found to be helpful in holding or positioning the connector where the flexible tube 16 is forced into the tubular portion 12. This flange 18 is also used in a similar manner when one end of an endotracheal tube 20 is forced onto the tubular or outlet portion 14.

The outside diameter of the gas outlet portion 14 is reduced in a tapered outlet end-portion 22 which begins at a circumferential line 24 around the outlet portion 14. This tapered outlet end-portion facilitates insertion of the connector 10 into the endotracheal tube 20 and provides for a smooth, turbulent-free, flow of oxygen or other gas from the connector and into the endotracheal tube 20.

As shown in FIG. 2, the inlet portion 12 slightly compresses the tube 16, which may cause some turbulence in the flow of oxygen or other gas.

As shown more clearly in FIG. 2, the connector 10 includes an intermediate portion 30, which defines a radially flared, axially extending, annular passageway 32 which is referred to, for convenience, as a generally cone-shaped or funnel-shaped passageway. The passageway 32 shares a common longitudinal axis with the tubular portion 12 and 14 and connects the interiors thereof. The funnel-shaped passageway 32 provides an elongated taper which forms an interior angle with respect to the longitudinal axis of between about 30° and 50°, and preferably about 45°. This reference to the interior angle is based on extrapolating the wall of the funnel-shaped passageway to the longitudinal axis of the connector or to an extension of the wall of the interior passageway of outlet 14, and is shown as angle alpha in FIG. 2.

The intermediate portion 30 also includes a shoulder 34 which lies adjacent to the base, or larger end, of the generally funnel-shaped passageway 32. Shoulder 34 has a width which is approximately equal to the wall thickness of the flexible tube 16. Therefore, when the flexible tube 16 is forced into the tubular portion 12 with its end abutting shoulder 34, the outer edge of the funnel-shaped passageway 32 is flush with the interior passage provided by flexible tube 16. This arrangement provides for a relatively unobstructed, turbulent-free flow of gas with a minimal effort by an intubated patient.

In applicant's device, the tubular portion 14 also includes an enlarged segment 14', which provides additional structural support between the tubular portion 14 and the tubular portion 12. The enlarged segment 14' is downstream from flange 18 and avoids structural weakness which might have been caused by the elongated funnel-shaped passageway 32.

Applicant's connectors may be produced from any suitable rigid or semi-rigid material, as will be understood by those skilled in the art. However, in its preferred form, the connectors are molded as a one-piece element from a thermoplastic, such as nylon, polyethylene or polypropylene.

The effects on the work of breathing over the inspiration and expiration portions of the breathing cycle are illustrated by the following table, wherein the endotracheal tubes are commonly available tubes and the standard adapters are those which are furnished with those tubes. Standard adapters are the 8 mm, 7.5 mm and 7.0 mm adapters. The adapters, identified as "long Pell," are in accordance with my previously mentioned U.S. Pat. No 4,919,127, while the "short Pell" refers to the adapters in accordance with the present invention. The test results were obtained by using a testing apparatus disclosed in a U.S. Patent of Hoyt, et al., U.S. Pat. No. 5,473,954, entitled "Apparatus for Testing Pulmonary Devices."

| Tracheal Tube Adapter | Test Series # | Peak Inhale Pressure (mmHg) | % Difference vs. 8 mm | Peak Exhale Pressure (mmHg) | % Difference vs. 8 mm | Peak Inhale Pressure (mmHg) |
|---|---|---|---|---|---|---|
| 30 Breaths/Minute | | 0.4 Liter Tidal Volume | | | | |
| Short Pell | 20,10,1 | −0.64 | −7.7 | 0.69 | 13.0 | |
| Long Pell | 93,94,95 | −0.67 | −3.8 | 0.85 | 39.1 | |
| 8.0 mm | 50,51,53 | −0.69 | — | 0.61 | — | |
| 7.5 mm | 118,119,120 | −0.93 | 34.6 | 1.20 | 95.7 | |
| 7.0 mm | 72,75,77 | −1.13 | 63.5 | 1.13 | 84.8 | |
| 30 Breaths/Minute | | 0.6 Liter Tidal Volume | | | | |
| Short Pell | 20,10,1 | −1.60 | −4.0 | 1.33 | 5.3 | −3.06 |
| Long Pell | 93,94,95 | −1.60 | −4.0 | 1.73 | 36.8 | −2.93 |
| 8.0 mm | 50,51,53 | −1.66 | — | 1.26 | — | −2.99 |
| 7.5 mm | 118,119,120 | −2.26 | 36.0 | 2.53 | 100.0 | −3.99 |
| 7.0 mm | 72,75,77 | −2.73 | 64.0 | 2.39 | 89.5 | −4.66 |
| 40 Breaths/Minute | | 0.4 Liter Tidal Volume | | | | |
| Short Pell | 24,14,4 | −1.20 | −10.0 | 1.13 | 6.3 | |
| Long Pell | 98,97,96 | −1.26 | −5.0 | 1.46 | 37.5 | |
| 8.0 mm | 69,68,67 | −1.33 | — | 1.06 | — | |
| 7.5 mm | 123,122,121 | −1.73 | 30.0 | 2.00 | 87.5 | |
| 7.0 mm | 73,76,79 | −2.13 | 60.0 | 1.86 | 75.0 | |
| 40 Breaths/Minute | | 0.6 Tidal Volume | | | | |
| Short Pell | 24,14,4 | −2.79 | −10.6 | 2.26 | 6.3 | −5.19 |
| Long Pell | 98,97,96 | −2.93 | −6.4 | 2.93 | 37.5 | −5.05 |
| 8.0 mm | 69,68,67 | −3.13 | — | 2.13 | — | −5.59 |
| 7.5 mm | 123,122,121 | −3.99 | 27.7 | 4.39 | 106.3 | −6.92 |
| 7.0 mm | 73,76,79 | −4.79 | 53.2 | 4.26 | 100.0 | −8.51 |
| 40 Breaths/Minute | | 1.5 Liter Tidal Volume | | | | |
| Short Pell | 1 | −17.29 | −3.7 | 16.63 | 31.6 | |
| Long Pell | 4 | −17.29 | −3.7 | 13.97 | 10.5 | |
| 8.0 mm | 7 | −17.96 | — | 12.64 | 0.0 | |
| 7.5 mm | 10 | −22.61 | 25.9 | 27.93 | 121.1 | |

Set-Up: Adapter alone (no "TEE")

Prior to the development of applicant's improved method for optimizing the breathing ability of a patient, there was little or no consideration given to the effect of increasing or decreasing the work associated with the expiration of air from a patient's lungs. In effect, it was recognized that patients die because of an inability to draw air and/or oxygen into the lungs. The expiration of the air was taken for granted, that is, the elasticity of the lungs would push the air out of the lungs. However, it has now been recognized that a slight increase in the work required for expiration of the air can have a significant effect on the patient's blood chemistry. For example, a slight increase in the work of expiration results in an increase in the absorption of oxygen and/or medication by the lungs.

The second embodiment of the invention, which is illustrated in FIG. 3, is generally similar to the preferred embodiment. However, in the second embodiment, a generally funnel-shaped passageway 52 defines a concave arcuate surface of revolution.

Figure 4:
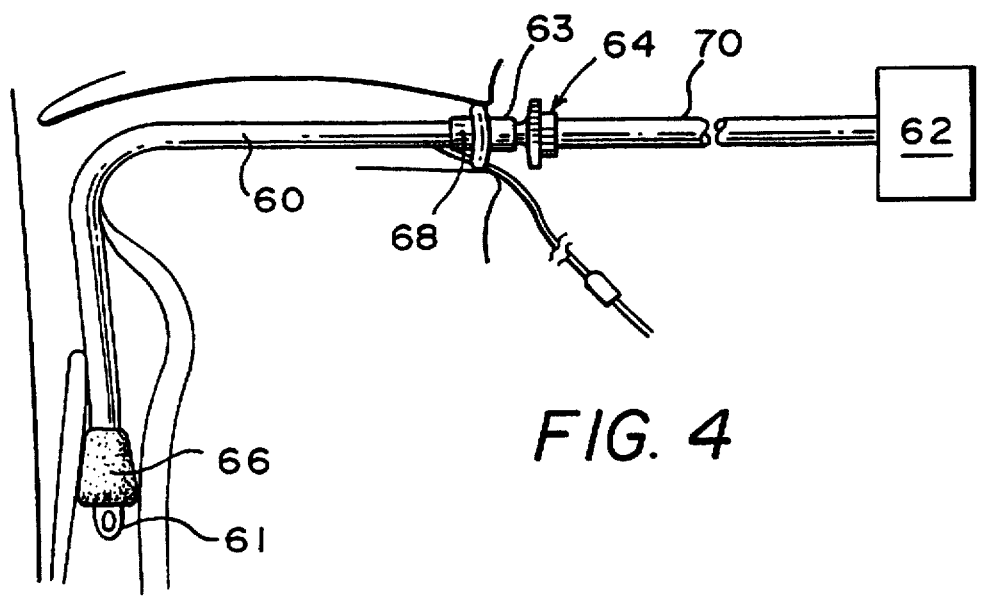
FIG. 4 is a side elevational view showing a combination of an endotracheal tube, source of oxygen and a connector in accordance with the present invention.
Figure 5:
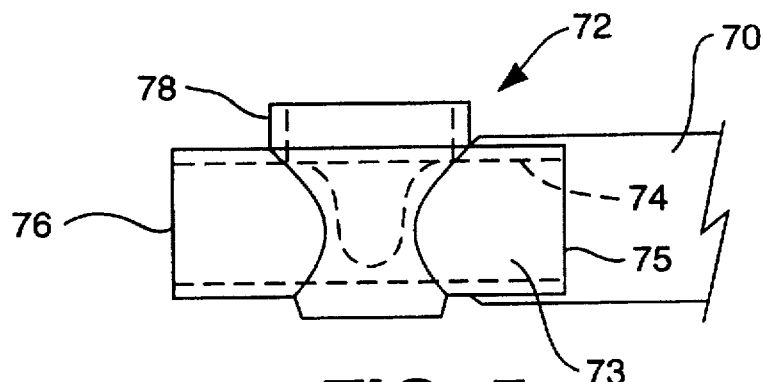
FIG. 5 is a side elevational view of a T-shaped adapter, in accordance with a preferred embodiment of the invention.
Figure 6:
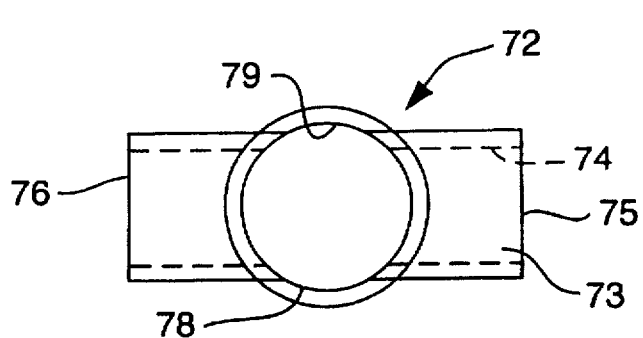
FIG. 6 is a top or plan view of the T-shaped adapter shown in FIG. 5.
Figure 7:
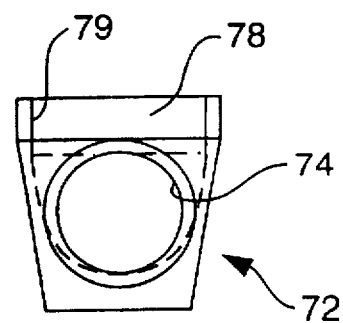
FIG. 7 is an end view of the T-shaped adapter shown in FIGS. 5 and 6.

FIG. 4 illustrates a combination of an endotracheal tube 60, source of oxygen or other gas 62, a T-shaped adapter 72 and connector 10. In this combination, the endotracheal tube 60 includes a distal end 61 adapted for intubation in a patient and a proximal end 63 which is adapted to protrude from an intubated patient's mouth or nose. The endotracheal tube 60 also includes an inflatable cuff 66 at the distal end 61. The details of the inflatable cuff and a bite block (not shown) are disclosed in my earlier U.S. Pat. Nos. 4,850,348 and 4,919,127.

The connector 10 shown in FIG. 4 has the same configuration as shown in FIG. 2 and is connected to the T-shaped adapter 72 and source of oxygen 62 by a flexible tube 70.

A connector 10, is particularly applicable for use in combination with a T-shaped adapter 72, which is shown in FIGS. 4–8. As illustrated in FIGS. 1–3, the connector 10 is an integral one-piece molded plastic element, which includes tubular portions 12 and 14, which share a common longitudinal axis (not shown). The connector 10 also includes an intermediate portion 30 which defines a funnel-like passageway 42. This funnel-like passageway 42 may be defined as a generally S-shaped surface of revolution which connects the portion 12 with portion 14. In other words, the passageway 42 may be described as having a smooth, generally S-shaped cross-section which is rotated about the passageway's central axis. This passageway provides a smooth transition as a gas passes from portion 12 to portion 14 in response to a patient's drawing of a breath, i.e., during the inspiration portion of the breathing cycle—in other words, when the patient inhales.

The T-shaped adapter 72 shown in FIGS. 5–8 includes a first portion 73 which defines a first cylindrical passageway 74, or smooth bore, which extends therethrough from a first end 75 to a second end 76. This first portion 73 is analogous to the cross-member of the T. The T-shaped connector 72 also includes a second portion 78 which is analogous to the vertical intersecting member of the T. The second portion 78 defines a second cylindrical passageway 79, which intersects with and connects it with the first cylindrical passageway 74. The second cylindrical passageway 79 also has a slightly larger diameter than the first cylindrical passageway 74.

Figure 8:
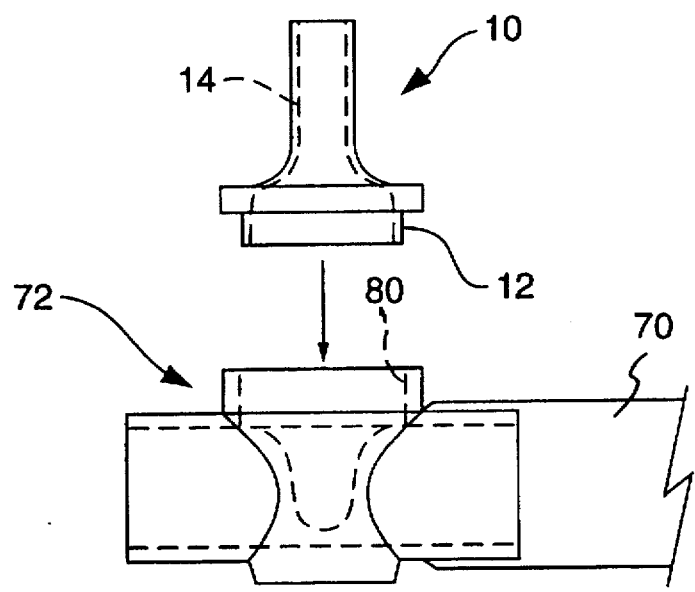
FIG. 8 is a side elevational view showing the T-shaped adapter and connector which shows how they fit together.

The second portion 78 also includes coupling means such as a female receptor 80 for coupling the T-shaped adapter 72 and connector 10, as shown in FIG. 8. As shown, the portion 12 of connector 10 has an outside diameter which is slightly less than the inside diameter of passageway 79. For example, in the preferred embodiment of the invention, the maximum outside diameter of the portion 12 of connector 10 is one inch, or slightly less. By contrast, the inside diameter of the second portion 78 of the T-shaped adapter has an inside diameter of nominally one inch or slightly greater, and an outside diameter of about 1.180 inches which provides a tight fit and a relatively thin wall section.

It has also been found that the combination of an endotracheal tube connector and T-shaped adapter, in accordance with the present invention, results in a dramatic reduction in the work for inspiration (inhaling) by a patient, as compared to the work which is required for a conventional connector-T-shaped adapter combination. The following tables illustrate the reduction in work and effect on peak pressures.

| Endotracheal (ET) Tube & Set-Up | Note # | WORK OF BREATHING | | | |
|---|---|---|---|---|---|
| | | Exhale Work (Nm) | % Difference vs. Ref. | Inhale Work (Nm) | % Difference vs. Ref. |
| 16 Breaths/Minute | | 0.4 Liter Tidal Volume | | | |
| Pell ET Tube | 1 | 0.028 | −3.4 | 0.024 | −4.0 |
| Pell w/TEE | 2 | 0.009 | −69.0 | 0.007 | −72.0 |
| Ref. w/TEE | 3 | 0.027 | −6.9 | 0.027 | 8.0 |
| Ref. ET Tube | 4 | 0.029 | — | 0.025 | — |
| 16 Breaths/Minute | | 0.6 Liter Tidal Volume | | | |
| Pell ET Tube | 1 | 0.082 | 0.0 | 0.073 | 0.0 |
| Pell w/TEE | 2 | 0.036 | −56.1 | 0.030 | −58.9 |
| Ref. w/TEE | 3 | 0.077 | −6.1 | 0.076 | 4.1 |
| Ref. ET Tube | 4 | 0.082 | — | 0.073 | — |
| 16 Breaths/Minute | | 0.8 Liter Tidal Volume | | | |
| Pell ET Tube | 1 | 0.176 | 2.3 | 0.162 | 3.8 |
| Pell w/TEE | 2 | 0.092 | −46.5 | 0.079 | −49.4 |
| Ref. w/TEE | 3 | 0.166 | −3.5 | 0.163 | 4.5 |
| Ref. ET Tube | 4 | 0.172 | — | 0.156 | — |
| 24 Breaths/Minute | | 0.4 Liter Tidal Volume | | | |
| Pell ET Tube | 1 | 0.054 | 0.0 | 0.049 | 0.0 |
| Pell w/TEE | 2 | 0.017 | −68.5 | 0.014 | −71.4 |
| Ref. w/TEE | 3 | 0.051 | −5.6 | 0.051 | 4.1 |
| Ref. ET Tube | 4 | 0.054 | — | 0.049 | — |
| 24 Breaths/Minute | | 0.6 Liter Tidal Volume | | | |
| Pell ET Tube | 1 | 0.164 | 3.1 | 0.151 | 4.1 |
| Pell w/TEE | 2 | 0.065 | −59.1 | 0.058 | −61.4 |
| Ref. w/TEE | 3 | 0.153 | −3.8 | 0.151 | 4.1 |
| Ref. ET Tube | 4 | 0.159 | — | 0.145 | — |
| 24 Breaths/Minute | | 0.8 Liter Tidal Volume | | | |
| Pell ET Tube | 1 | 0.360 | 5.3 | 0.337 | 6.3 |
| Pell w/TEE | 2 | 0.193 | −43.6 | 0.166 | −47.6 |
| Ref. w/TEE | 3 | 0.333 | −2.6 | 0.331 | 4.4 |
| Ref. ET Tube | 4 | 0.342 | — | 0.317 | — |
| 32 Breaths/Minute | | 0.4 Liter Tidal Volume | | | |
| Pell ET Tube | 1 | 0.087 | 0.0 | 0.080 | 2.6 |
| Pell w/TEE | 2 | 0.028 | −67.8 | 0.024 | −69.2 |
| Ref. w/TEE | 3 | 0.082 | −5.7 | 0.081 | 3.8 |
| Ref. ET Tube | 4 | 0.087 | — | 0.078 | — |
| 32 Breaths/Minute | | 0.6 Liter Tidal Volume | | | |
| Pell ET Tube | 1 | 0.268 | 4.3 | 0.252 | 5.9 |
| Pell w/TEE | 2 | 0.100 | −61.1 | 0.086 | −63.9 |
| Ref. w/TEE | 3 | 0.250 | 2.7 | 0.248 | 4.2 |
| Ref. ET Tube | 4 | 0.257 | — | 0.238 | — |
| 32 Breaths/Minute | | 0.8 Liter Tidal Volume | | | |
| Pell ET Tube | 1 | 0.606 | 6.5 | 0.569 | 7.8 |
| Pell w/TEE | 2 | 0.396 | −30.4 | 0.344 | −34.8 |
| Ref. w/TEE | 3 | 0.558 | −1.9 | 0.552 | 4.5 |
| Ref. ET Tube | 4 | 0.569 | — | 0.528 | — |
| 40 Breaths/Minute | | 0.4 Liter Tidal Volume | | | |
| Pell ET Tube | 1 | 0.129 | 1.6 | 0.121 | 3.4 |
| Pell w/TEE | 2 | 0.044 | −65.4 | 0.038 | −67.5 |
| Ref. w/TEE | 3 | 0.121 | −4.7 | 0.121 | 3.4 |
| Ref. ET Tube | 4 | 0.127 | — | 0.117 | — |
| 40 Breaths/Minute | | 0.6 Liter Tidal Volume | | | |
| Pell ET Tube | 1 | 0.404 | 5.5 | 0.380 | 7.3 |
| Pell w/TEE | 2 | 0.141 | −63.2 | 0.122 | −65.5 |
| Ref. w/TEE | 3 | 0.375 | −2.1 | 0.371 | 4.8 |
| Ref. ET Tube | 4 | 0.383 | — | 0.354 | — |
| 40 Breaths/Minute | | 0.8 Liter Tidal Volume | | | |
| Pell ET Tube | 1 | 0.912 | 6.8 | 0.857 | 8.2 |
| Pell w/TEE | 2 | 0.633 | −25.9 | 0.560 | −29.3 |
| Ref. w/TEE | 3 | 0.837 | −2.0 | 0.827 | 4.4 |
| Ref. ET Tube | 4 | 0.854 | — | 0.792 | — |

-continued

PEAK PRESSURES

| Endotracheal (ET) Tube & Set-Up | Note # | Peak Exhale Pressure (cmH2O) | % Difference vs. Ref. | Peak Inhale Pressure (cmH2O) | % Difference vs. Ref. |
|---|---|---|---|---|---|
| 16 Breaths/Minute | | | 0.4 Liter Tidal Volume | | |
| Pell ET Tube | 1 | 1.0 | 0.0 | −0.9 | 0.0 |
| Pell w/TEE | 2 | 0.3 | −70.0 | −0.2 | −77.8 |
| Ref. w/TEE | 3 | 0.9 | −10.0 | −0.9 | 0.0 |
| Ref. ET Tube | 4 | 1.0 | — | −0.9 | — |
| 16 Breaths/Minute | | | 0.6 Liter Tidal Volume | | |
| Pell ET Tube | 1 | 1.9 | −5.0 | −1.7 | 0.0 |
| Pell w/TEE | 2 | 0.8 | −60.0 | −0.7 | −58.8 |
| Ref. w/TEE | 3 | 1.8 | −10.0 | −1.8 | 5.9 |
| Ref. ET Tube | 4 | 2.0 | — | −1.7 | — |
| 16 Breaths/Minute | | | 0.8 Liter Tidal Volume | | |
| Pell ET Tube | 1 | 3.3 | 3.1 | −3.0 | 7.1 |
| Pell w/TEE | 2 | 1.7 | −46.9 | −1.5 | −46.4 |
| Ref. w/TEE | 3 | 3.1 | −3.1 | −3.0 | 7.1 |
| Ref. ET Tube | 4 | 3.2 | — | −2.8 | — |
| 24 Breaths/Minute | | | 0.4 Liter Tidal Volume | | |
| Pell ET Tube | 1 | 1.9 | 0.0 | −1.8 | 5.9 |
| Pell w/TEE | 2 | 0.5 | −73.7 | −0.5 | −70.6 |
| Ref. w/TEE | 3 | 1.8 | −5.3 | −1.8 | 5.9 |
| Ref. ET Tube | 4 | 1.9 | — | −1.7 | — |
| 24 Breaths/Minute | | | 0.6 Liter Tidal Volume | | |
| Pell ET Tube | 1 | 4.0 | 2.6 | −3.7 | 2.8 |
| Pell w/TEE | 2 | 1.6 | −59.0 | −1.4 | −61.1 |
| Ref. w/TEE | 3 | 3.8 | −2.6 | −3.7 | 2.8 |
| Ref. ET Tube | 4 | 3.9 | — | −3.6 | — |
| 24 Breaths/Minute | | | 0.8 Liter Tidal Volume | | |
| Pell ET Tube | 1 | 6.6 | 6.5 | −6.2 | 8.8 |
| Pell w/TEE | 2 | 3.5 | −43.5 | −3.0 | −47.4 |
| Ref. w/TEE | 3 | 6.1 | −1.6 | −6.0 | 5.3 |
| Ref. ET Tube | 4 | 6.2 | — | −5.7 | — |
| 32 Breaths/Minte | | | 0.4 Liter Tidal Volume | | |
| Pell ET Tube | 1 | 3.2 | 3.2 | −3.0 | 7.1 |
| Pell w/TEE | 2 | 1.0 | −67.7 | −0.9 | −67.9 |
| Ref. w/TEE | 3 | 2.9 | −6.5 | −2.9 | 3.6 |
| Ref. ET Tube | 4 | 3.1 | — | −2.8 | — |
| 32 Breaths/Minute | | | 0.6 Liter Tidal Volume | | |
| Pell ET Tube | 1 | 6.6 | 4.8 | −6.2 | 6.9 |
| Pell w/TEE | 2 | 2.4 | −61.9 | −2.1 | −63.8 |
| Ref. w/TEE | 3 | 6.1 | −3.2 | −6.0 | 3.4 |
| Ref. ET Tube | 4 | 6.3 | — | −5.8 | — |
| 32 Breaths/Minute | | | 0.8 Liter Tidal Volume | | |
| Pell ET Tube | 1 | 11.4 | 7.5 | −10.5 | 8.2 |
| Pell w/TEE | 2 | 7.4 | −30.2 | −6.4 | −34.0 |
| Ref. w/TEE | 3 | 10.3 | −2.8 | −10.2 | 5.2 |
| Ref. ET Tube | 4 | 10.6 | — | −9.7 | — |
| 40 Breaths/Minute | | | 0.4 Liter Tidal Volume | | |
| Pell ET Tube | 1 | 4.8 | 4.3 | 4.5 | 4.7 |
| Pell w/TEE | 2 | 1.6 | −65.2 | −1.4 | −67.4 |
| Ref. w/TEE | 3 | 4.4 | −4.3 | 4.4 | 2.3 |
| Ref. ET Tube | 4 | 4.6 | — | −4.3 | — |
| 40 Breaths/Minute | | | 0.6 Liter Tidal Volume | | |
| Pell ET Tube | 1 | 10.1 | 6.3 | −9.4 | 8.0 |
| Pell w/TEE | 2 | 3.6 | −62.1 | −3.0 | −65.5 |
| Ref. w/TEE | 3 | 9.3 | −2.1 | −9.1 | 4.6 |
| Ref. ET Tube | 4 | 9.5 | — | −8.7 | — |
| 40 Breaths/Minute | | | 0.8 Liter Tidal Volume | | |
| Pell ET Tube | 1 | 17.2 | 8.2 | −15.8 | 9.0 |
| Pell w/TEE | 2 | 11.9 | −25.2 | −10.4 | −28.3 |
| Ref. w/TEE | 3 | 15.5 | −2.5 | −15.1 | 4.1 |
| Ref. ET Tube | 4 | 15.9 | — | −14.5 | — |

Set-Up: Endotracheal (ET) Tubes immersed in 37 degree C. Water Bath
NOTES:
1. Pell ET Tube alone.
2. Pell ET Tube with molded Pell Adapter and molded Pell TEE.
3. Ref. ET Tube with std. Adapter and std. TEE (with internal chimney).
4. Ref. ET Tube alone.

While the present invention has been described in connection with its preferred embodiments, it should be understood that changes and modifications may be made therein without departing from the scope of the appended claims.

What is claimed is:

1. A method for optimizing the breathing ability of an intubated patient comprising the steps of:
   (a) providing an endotracheal tube and a connector for connecting the endotracheal tube to a source of oxygen or other gas;
   (b) intubating the patient with the endotracheal tube; and
   (c) connecting the endotracheal tube to a source of oxygen or other gas by a connector which minimizes the inspirational work of the patient and increases the expirational work of the patient.

2. A method for optimizing the breathing ability of an intubated patient in accordance with claim 1 wherein the connector reduces the inspirational work of the patient as compared to a conventional connector and increases the expirational work of a patient as compared to a conventional connector.

3. A method for optimizing the breathing ability of an intubated patient according to claim 1 which includes the steps of:
   (d) providing an endotracheal tube and a connector for connecting the endotracheal tube to a source of oxygen or other gas;
   (e) evaluating the expirational flow characteristics of the connector;
   (f) selecting an endotracheal tube connector based on its expirational flow characteristics; and
   (g) connecting the endotracheal tube to the source of oxygen or other gas with the selected connector.

4. A method for optimizing the breathing ability of an intubated patient in accordance with claim 3 which includes the steps of evaluating the flow characteristics of the connector, based on the inspirational flow characteristics and selecting the connector, based on the inspirational flow characteristics.

5. A method for optimizing the breathing ability of an intubated patient in accordance with claim 4 in which the connector is selected to increase the expirational work of the patient.

6. A method for optimizing the breathing ability of an intubated patient in accordance with claim 5, in which the connector is selected to minimize the inspirational work of the patient.

7. A connector for connecting an endotracheal tube to a source of gas, comprising an annular gas inlet and an annular gas outlet sharing a common longitudinal axis with said inlet, and with said outlet extending downstream from said inlet, said inlet having an inside diameter which is about 2-¼ to 2-¾ times greater than the inside diameter of said outlet, and adapted to receive a flexible tube having an outside diameter which is approximately the same as the inside diameter of said inlet, and an intermediate portion between said inlet and said outlet defining a radially flared, outwardly extending annular passageway sharing a common longitudinal axis with said inlet and said outlet and connecting said inlet and said outlet with the smaller end of said radially flared passageway adjacent to the inside of said outlet, means for minimizing turbulence and thereby reducing the work of breathing, including a shoulder adjacent to the larger end of said radially flared passageway, said shoulder having a width approximately equal to the wall thickness of the flexible tube, so that when the flexible tube is inserted into the inside of said inlet, with its end abutting said shoulder, the outer edge of the large end of said radially flared passageway is flush with the interior passage provided by the flexible tube to thereby provide a smooth, unobstructed flow of gas through the tube and the connector, and a patient end-portion of said outlet sharing a common longitudinal axis with said cylindrical outlet means, and extending downstream therefrom, said patient end-portion having a tapered outside diameter terminating at a thin, circular leading edge so that one end of an endotracheal tube, which extends outside of the patient, can be forced over the tapered portion of the outlet to provide a relatively smooth, obstruction-free passageway from and through the connector to the endotracheal tube, whereby the work of inspiration by an intubated patient is minimized, and said connector also including means for increasing the expirational work of the patient.

8. A connector for connecting an endotracheal tube to a source of gas, according to claim 7, in which said means for increasing the expirational work of the patient comprises a relatively short annular gas inlet which has a length which is less than its diameter.

9. A connector for connecting an endotracheal tube to a source of gas, according to claim 8, in which said short annular gas inlet has a length which is between about ¼ to ⅓ of its diameter.

10. The combination of a connector and a T-shaped adapter for connecting an endotracheal tube to a source of gas, said combination including a connector having an annular gas inlet, an annular gas outlet, sharing a common longitudinal axis with said inlet, and with said outlet extending downstream from said inlet, said inlet having an inside diameter which is about 2-¼ to about 2-¾ times greater than the inside diameter of said outlet, and an intermediate portion between said inlet and said outlet defining a radially flared, outwardly extending annular passageway sharing a common longitudinal axis with said inlet and said outlet, and connecting said inlet and said outlet with the smaller end of said radially flared passageway adjacent to the inside of said outlet, and a T-shaped adapter having a first portion which defines a first cylindrical passageway extending therethrough and a second portion defining a second cylindrical passageway which intersects with and extends into said first cylindrical passageway, said second portion also including coupling means for coupling said second portion of said T-shaped adapter to said inlet of said connector for minimizing turbulence caused by a gaseous media passing therethrough to thereby reduce the work of inspiration by a patient, at the same time slightly increasing the work of expiration.

11. The combination of claim 10, wherein said coupling means comprises a force-fit, and wherein said inlet has an inside diameter of about 2.5 times greater than the inside diameter of said outlet.

12. The combination of claim 11, in which said annular inlet of said connector fits inside of said coupling means and provides a smooth surface for the flow of gas therethrough.

13. The combination of claim 12, wherein said annular gas inlet has a height which is equal to about 0.4 times its inside diameter and a wall thickness of less than 0.080 inches.

* * * * *